United States Patent [19]
Krahn et al.

[11] 4,145,123
[45] Mar. 20, 1979

[54] PERIMETER

[75] Inventors: Wilhelm E. Krahn, Hamburg; Manfred Born, Munich, both of Fed. Rep. of Germany

[73] Assignee: Optische Werke G. Rodenstock, Fed. Rep. of Germany

[21] Appl. No.: 778,086

[22] Filed: Mar. 16, 1977

Related U.S. Application Data

[63] Continuation-in-part of Ser. No. 609,485, Sep. 2, 1975.

[30] Foreign Application Priority Data

Aug. 30, 1974 [DE] Fed. Rep. of Germany ....... 2441578

[51] Int. Cl.$^2$ ............................................. A61B 3/02
[52] U.S. Cl. ......................................... 351/24; 351/23
[58] Field of Search .................................... 351/24, 23

[56] References Cited

U.S. PATENT DOCUMENTS 3,288,546 11/1966 Gans ...................................... 351/24
3,664,732 5/1972 Lynn ................................... 351/24 X

*Primary Examiner*—Paul A. Sacher
*Attorney, Agent, or Firm*—Craig & Antonelli

[57] ABSTRACT

A perimeter for perimetric eye testing is provided with an electronic control mechanism for varying the brightness of the light signals in a preselected manner such that reproducibility of the examination can be achieved. An optical indicating arrangement is included to indicate the brightness values to the examiner, while the electronic control mechanism can further control an electronic recorder for recording the results of the examination.

27 Claims, 7 Drawing Figures

PERIMETER

This is a continuation-in-part of the application entitled PERIMETER by Wilhelm E. Krahn and Manfred Born, Ser. No. 609,485, filed Sept. 2, 1975; and the benefits accorded to this parent application is hereby claimed for all of the common subject matter which is incorporated herein by reference.

This invention relates to a perimeter having at least one projector for reproducing fixed or movable light signals of varying size and brightness on the inside of an approximately hemispherical projection area, wherein a number of filters are introduced into the projection beam path for purposes of brightness control, either individually or in groups. More particularly, the present invention provides an electronic control of the introduction of the filters into the projection light beam path such as to vary the brightness in a preselected manner.

In certain perimetric examinations, the ophthalmological examination of a testee is achieved by the introduction at various locations in the field of vision of successive light signals of increasing brightness. This examination determines the brightness value at which perception of the light signal is effected at respective locations in the field of vision of the testee. In such examinations, it has been contemplated to vary the brightness of such light signals by continuously changing the light intensity of the source of illumination, or by the stepwise insertion of filters into the projection beam path.

However, examinations conducted in this manner cannot be compared with one another because accurate and comparable examination results are not obtained without a precise maintenance of certain brightness stages and without a correlation of the chronological sequence during the increasing of the light signal brightness.

It is an object of this invention to provide in a perimetric examination a light signal, introduced at preselected locations of the field of vision, which light signal can be varied in brightness in exactly defined stages and associated with a specific defined interval of time.

This object is attained in accordance with the present invention by providing an electronic control of an electromechanical drive mechanism which progressively changes filters in the projection beam path to either increase or decrease the brightness of the projected light signals. The electronic control is constructed so that the forward operation, or the reverse operation, can take place in specific adjustable time intervals, and during each switching operation, a dark pause appears which also has a specific adjustable duration. The electronic control in accordance with the present invention provides an electronic circuit, controllable by an examiner, for controlling the drive of a drive motor in the electromechanical drive mechanism, which may be of a conventional servomotor type, to vary the introduction of the filters into the projected light beam paths.

This arrangement makes it possible to conduct examinations, as often as desired in a reproducible manner, wherein the examiner can vary the brightness of the light signal offered to the testee in a specific predetermined succession of points in the field of vision and at various brightness stages. In this manner it is possible to repeat an exactly defined examination with the same testee at different times, or to compare the test results between a plurality of testees and tabulate the results.

In a further embodiment of the present invention, the electronic control can be adapted to switch a predetermined number of filter stages in succession between the actual illumination and introduction of the test light signal to the testee. In this regard, the electronic control can effect the dark pause over a given period of time, during which the predetermined number of filter stages are stepwise switched in succession. For example, five filter stages can be switched in succession during the dark pause so that only each fifth filter stage is actually introduced into the light beam path for presentation to the testee. Such a multiple switching of filter stages between presentation of the light signal to the testee allows a time-saving preliminary examination of the testee. Furthermore, the electronic control can be adapted to carry out the multiple switching of filter stages during the reverse operation, as well as the forward operation.

This electronic control allows a predetermined filter value to be selected and a continuous switching effected, either rapidly forward or in reverse, in order to rapidly present a desired filter value.

A further object of this invention resides in a monitoring of the progress of the examination by an optical indicator which indicates each set or passing filter value.

This object is attained in accordance with the present invention by associating each filter value, which is introduced into the projection light beam path, with an optical indication observable by the examiner. The indication can be effected in a digital manner or with the aid of a scale and an indicator pointer. In a preferred manner, a numerical scale, containing the filter values to be set, can be provided on a control panel or desk wherein each filter value is associated with a light source being illuminated upon setting the respective filter value. Suitable light sources are light-emitting diodes. The numerical scale with its light sources associated with the individual numerical values can be arranged on or adjacent to a supporting surface for a printed diagram sheet of the type utilized in perimetric examinations. The scale of the printed diagram sheet corresponds to the graduations of the numerical scale with its associated light sources. In this connection, the printed diagram sheet can cover the individual light sources, and can have perforations associated with these light sources. This indication of the filter values can be easily observed even in darkened examining rooms without having deleterious effects on the ambient light conditions during the perimetric examinations.

In a further embodiment, the electronic control for the filter drive mechanism can be connected with an electronic recorder, or writer, which automatically records the measuring points and/or meridian circles into a diagram indicating the results of the perimetric examination. Thus, the location of the light signal presented to the testee can be automatically recorded, together with the brightness values corresponding to the preselected variation of filter stages.

The present invention may be further understood by reference to the drawing figures, which illustrate in non-limitative embodiments the features of the present invention.

Figure 1:
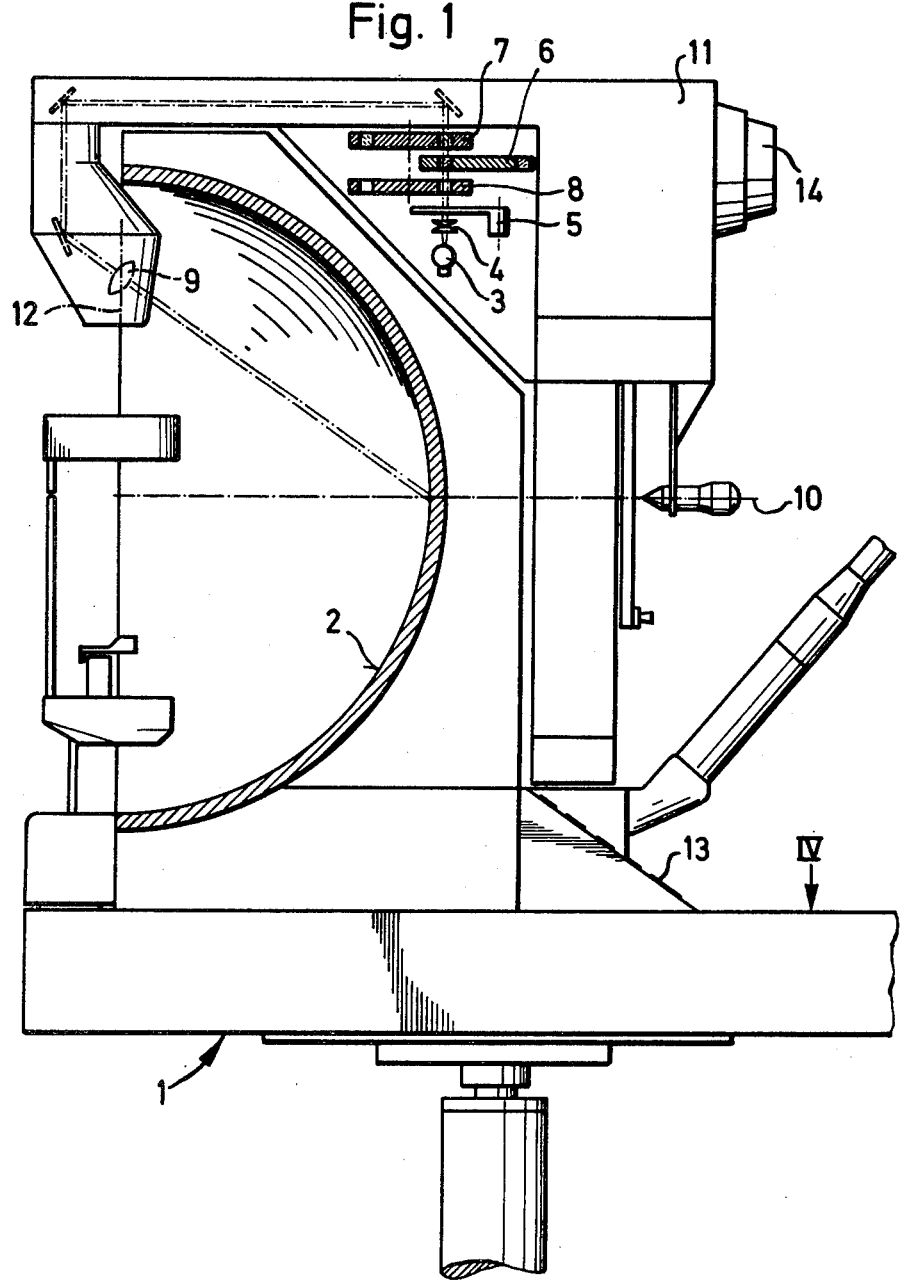
FIG. 1 shows a lateral view of a perimeter in partial section.

Reference to the drawing figures wherein the same reference numerals are utilized throughout to designate the same elements, FIG. 1 shows in detail a perimeter 1 with a hemispherical projection surface 2 for which the present invention may be utilized. This perimeter can be of a conventional type, such as a Rodenstock perimeter PHZ 74 model, available from G. Rodenstock Instrumente GMBH of Munchen, West Germany.

The projection arrangement for the perimeter light signal consists essentially of a light source 3, a condenser system 4, a mechanical shutter 5, filter disks 6 and 7, an apertured diaphragm 8, deflecting mirrors or prisms and a projection objective 9. This projection system is disposed in a projector holder 11 pivotal about the horizontal axis 10 wherein the projection objective is further pivotal about the axis 12 extending at right angles to the horizontal axis 10.

An electromechanical drive mechanism (not shown in this figure for purposes of clarity) is provided for operating the filter disks 6, 7, as well as the apertured diaphragm disk 8. This drive mechanism is electronically controlled in accordance with the present invention from the control desk 13. From this control desk 13, it is also possible to control the pivotal movement of the projector holder 11 about the horizontal axis 10, as well as the pivoting of the projecting objective 9 about the axis 12 with the aid of servomotors. These movements can also be effected manually with the aid of the operating knob 14.

Figure 2:
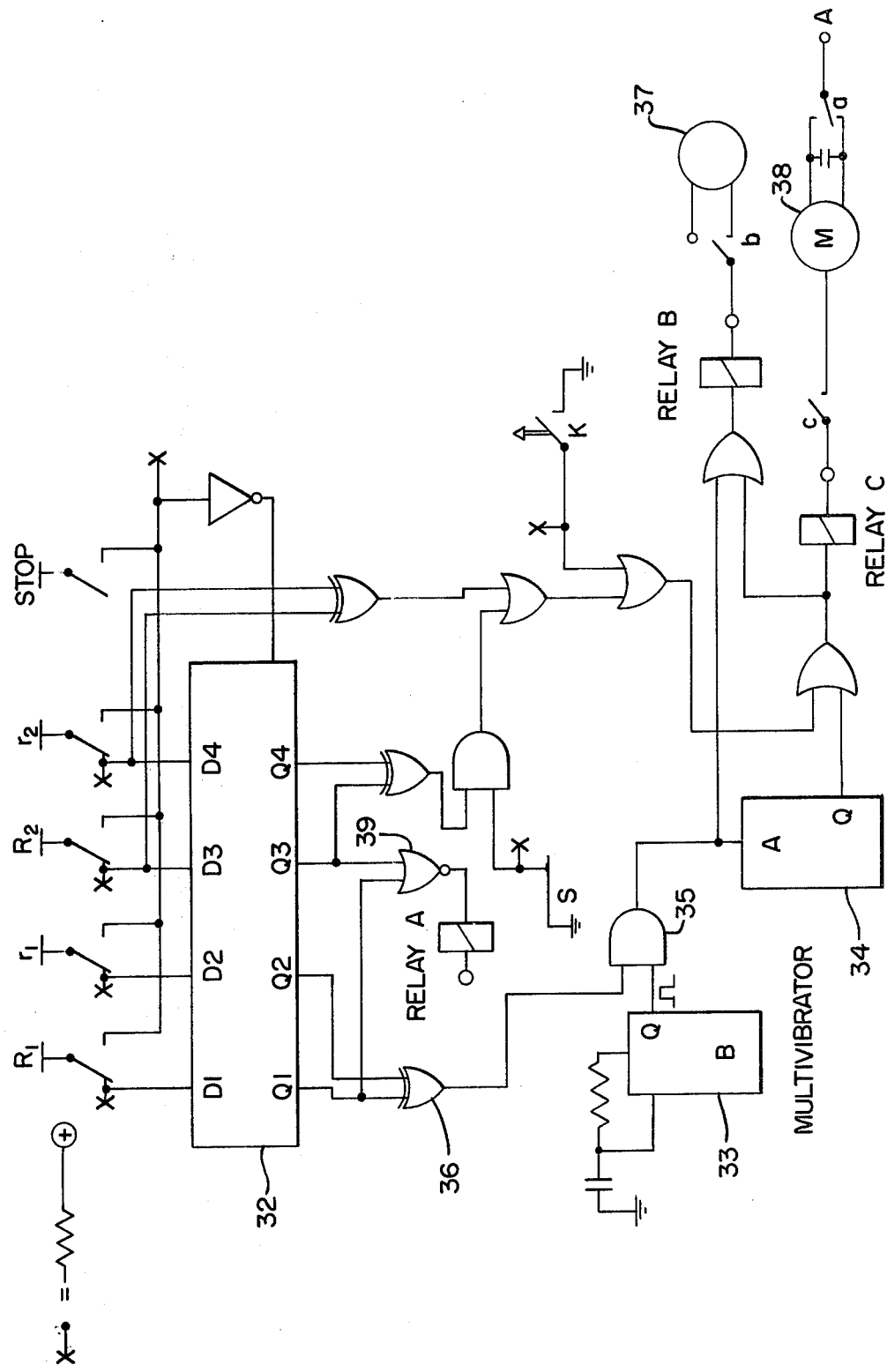
FIG. 2 shows a schematic circuit representation of the electronic control according to the present invention.

FIG. 2 shows a partial schematic circuit for the electronic control of the drive mechanism for switching the filters in the filter disks 6, 7 to vary the brightness of the projected light beam signal. In this circuit supplied through a voltage source at X, for example, the operation of the key button $R_1$ operates the flip-flop 32 by connection to the input D1 such that an output signal results at Q1. The multi-vibrator 33 is activated and provides a rectangular wave signal to the AND gate 35, which also receives at a second input the signal from the flip-flop 32 through an EXCLUSIVE OR gate 36. The AND gate 35 provides a signal to the relay B, which switches on a shutter for activating the bright and dark phases of the filter switching operation through contact b to operate step motor 37 at the frequency of the multi-vibrator 33.

A second multi-vibrator 34 is connected to provide an impulse to the relay C, which switches on the filter drive motor 38 through contact c. This relay assures operation of the motor until the next filter position. The output signal from Q1 of the flip-flop 32 may also switch relay A through NOR gate 39 for effecting reversal of the direction of rotation of the drive motor 38 by closing contact a, thereby reversing the selection of the filter stages.

The operation of the key button $r_2$ controls by the input D4 of flip-flop 32 the continuous switching through multiple stages of the filter stages during the dark period of the switching operation. Thus, the drive motor continues to run until the fifth filter disk, for example, is reached. By use of the sliding contact S, the drive motor, as well as the shutter providing the dark pause of the switching operation, remains in operation until the fifth filter stage is reached. A stop key "STOP" effects immediate interruption of the automatic switching, as well as the multiple stage switching.

In FIG. 2, contact $R_1$ (D1) activates the motor in continuous counterclockwise rotation, while contact $r_1$(D2) provides continuous clockwise rotation of the filter disk. The filters are switched for a predetermined time, while there is a dark pause, controlled by a rotary magnet, between the switched-on periods of the individual filters.

Contact $R_3$ (D3) activates the counterclockwise rotation in groups, and contact $r_2$ (D4) activates the clockwise rotation in groups of the filter disk, such that during a dark pause five filter stages pass. The filter disk remains ineffective upon reaching a preselected filter position until activation of one of the above cited contacts triggers another movement of the filter disk. The four contacts have to be activated individually.

Contact K interacts with a click stop device which rotates together with the filter disk and provides that the driving motor of the filter disk continues operating until reaching the next filter position, and then stops precisely in accordance with the click stop device.

Sliding contact S interacts with an indicator for light intensity values, and rotates with the filter disk. In case of step-by-step switching in groups of the filters, the contact S serves to stop the rotation of the filter disk after every five filter stages.

The flip-flop 32 represents an electronic interlocking switch system. D1 and D2 are responsible for the automatic filter movement. When D1 is activated the output Q1 is activated, and the relay C is switched on via gate 35.

The multi-vibrator 34 receives the rectangular wave signal from the output of gate 35 and transmits an abbreviated rectangular wave signal to relay C. This output signal activates the motor 38 via relay C. However, since the output signal is very brief and serves merely to start the motor, it is necessary to let the motor run by means of contact K until the following filter value has been accurately established. The motor drives the filter disk and is connected with a stop disk. Contact K can interrupt action of the stop disk. The stop mark is identical with the filter position. Contact K closes upon reaching the correct position.

Upon activation of D1 and D2, the motor operates in accordance with the prevailing rectangular wave signal until another key (for instance STOP) is pressed. Relay A (left or right switching of motor) is activated by pressing "1" (idle position = right hand key).

The multi-stage switch is activated from output D3 and D4. On an indicator of filter values rotating with the filter disk there are contact panels after every five steps with which contact S interacts. The motor will operate until reaching a stop mark. Precise positioning is secured via contact K and the stop disk. The indicator for filter values rotates together with the filter disk and supplies the signals concerning the filter values to the indicator diodes and transmits a signal to relay C after every five values.

Figure 3:
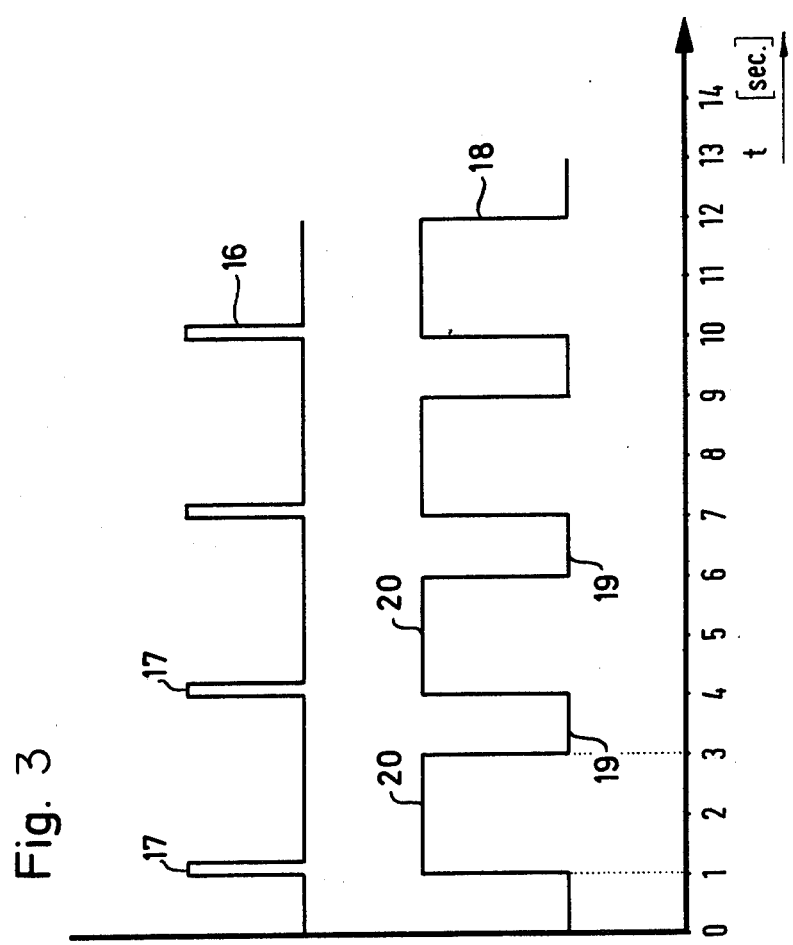
FIG. 3 shows a schematic representation of the individual light and dark periods in connection with a continued switching of individual filters.

FIG. 3 shows diagrammatically the switching of individual filter stages in accordance with the electronic control of FIG. 2. Namely, in cooperation with the illumination periods of the light signal, controlled by shutter 5 as a function of time, individual filter stages are switched during periods of dark and illumination. Thus, the continuous line 16 indicates at the upper level 17 a switching of the filter disks 7, 8, while the continuous line 18 represents the illumination intervals at the lower level 19, as well as the dark intervals at the upper level 20. Accordingly, in this diagram, the illumination intervals are respectively at a duration of one second, while the interposed dark periods amount to two seconds. Other time values are also possible within the scope of the electronic control of this invention.

Figure 4:
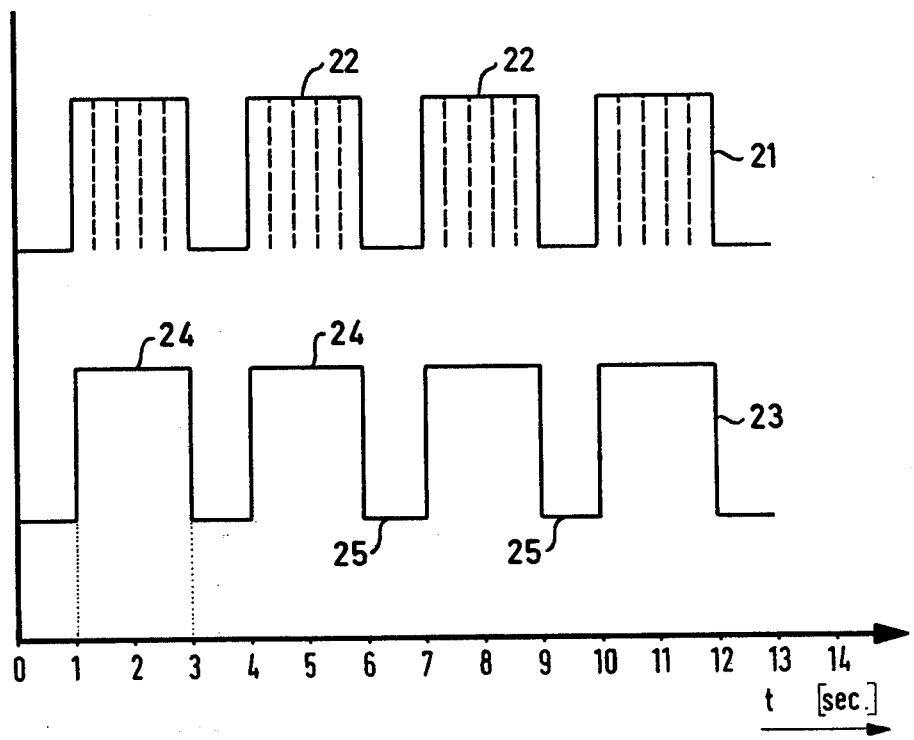
FIG. 4 shows a schematic view of the light and dark periods in conjunction with the continuous switching of filter groups.

FIG. 4 shows a similar diagram as that of FIG. 3, but with a multiple switching of filter groups during each dark interval between two illumination periods. Namely, five filter stages are rapidly switched in succession so that only each fifth filter stage is acutally used. The top line 21 shows the switching of the filters, wherein respectively at the upper level 22, five filters are switched in succession. The lower continuous line 23 shows at its upper level 24, the dark intervals during which the filters are switched. The lower level 25 of the continuous line 23 denote the illumination periods of the respectively set fifth filter.

Figure 5:
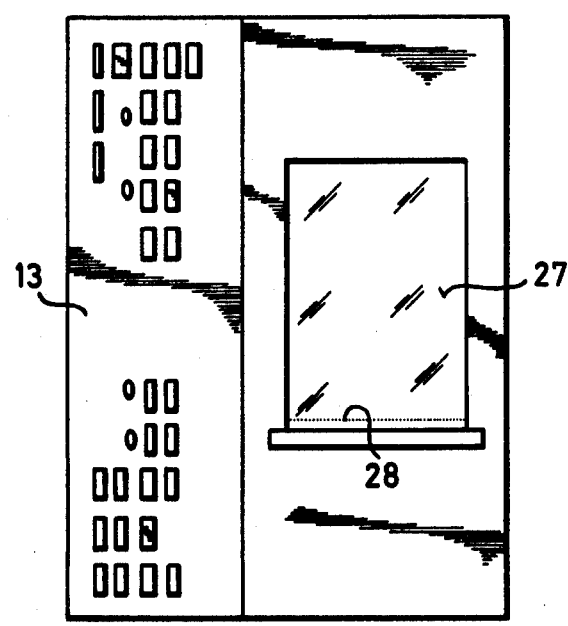
FIG. 5 shows the top view of the control panel or desk of the perimeter with the optical indicator for the filter stages.

FIG. 5 is a top view of the control desk 13 in the direction IV in FIG. 1. In front of the control desk is a supporting surface 27 which can be illuminated from below for a printed diagram sheet. In a side area of the supporting surface 27, an optical indicator 28 is provided constituted of individual light sources associated with the adjustable filter values to be actuated upon selection of the filter value in the projection light beam path.

Figure 6:
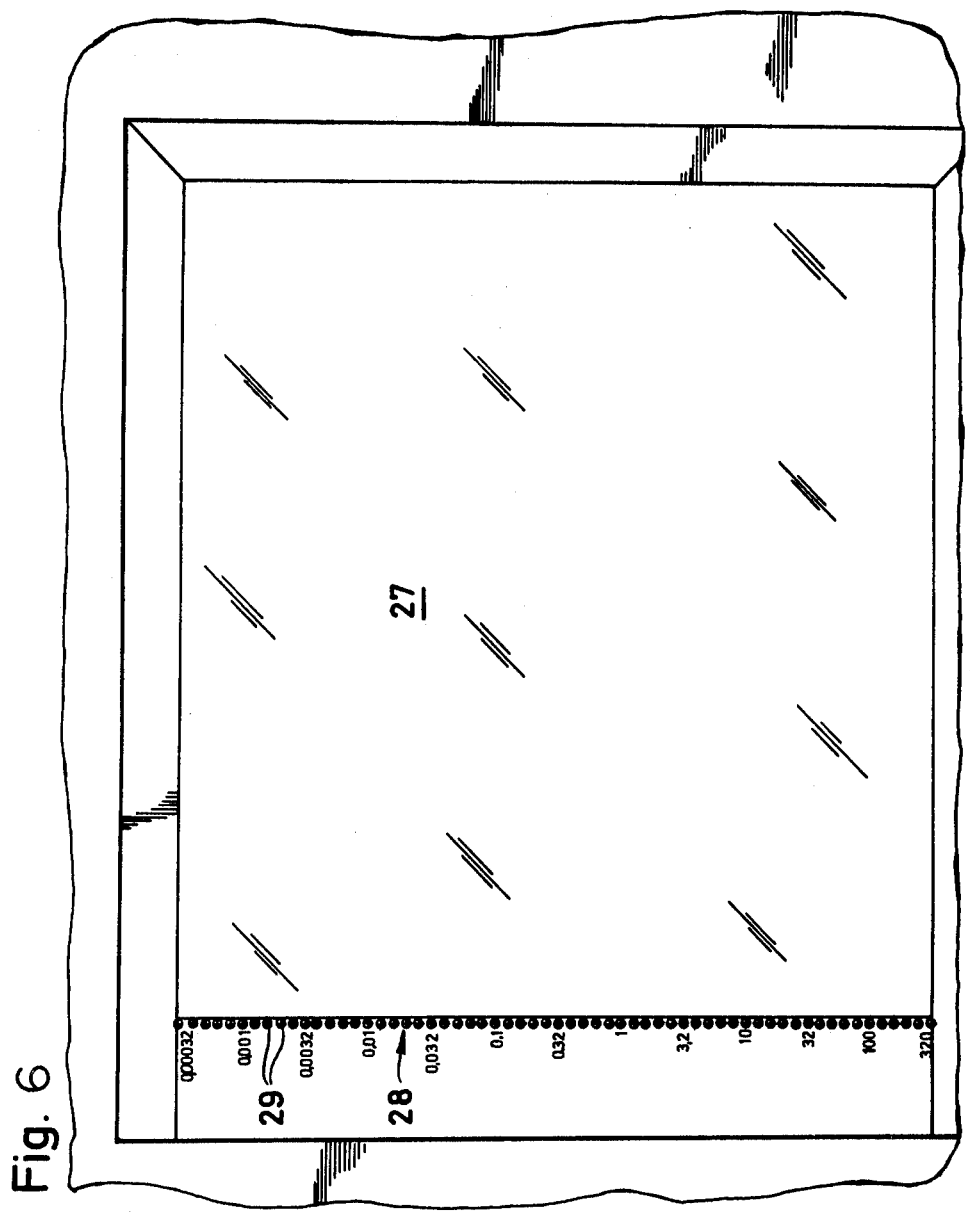
FIG. 6 shows the filter indicator of FIG. 5 on an enlarged scale.

FIG. 6 shows the supporting surface 27 of FIG. 5 on an enlarged scale. The optical indicator 28 consists of a plurality of light-emitting diodes 29 which correspond with a numerical scale indicating the individual filter values.

Figure 7:
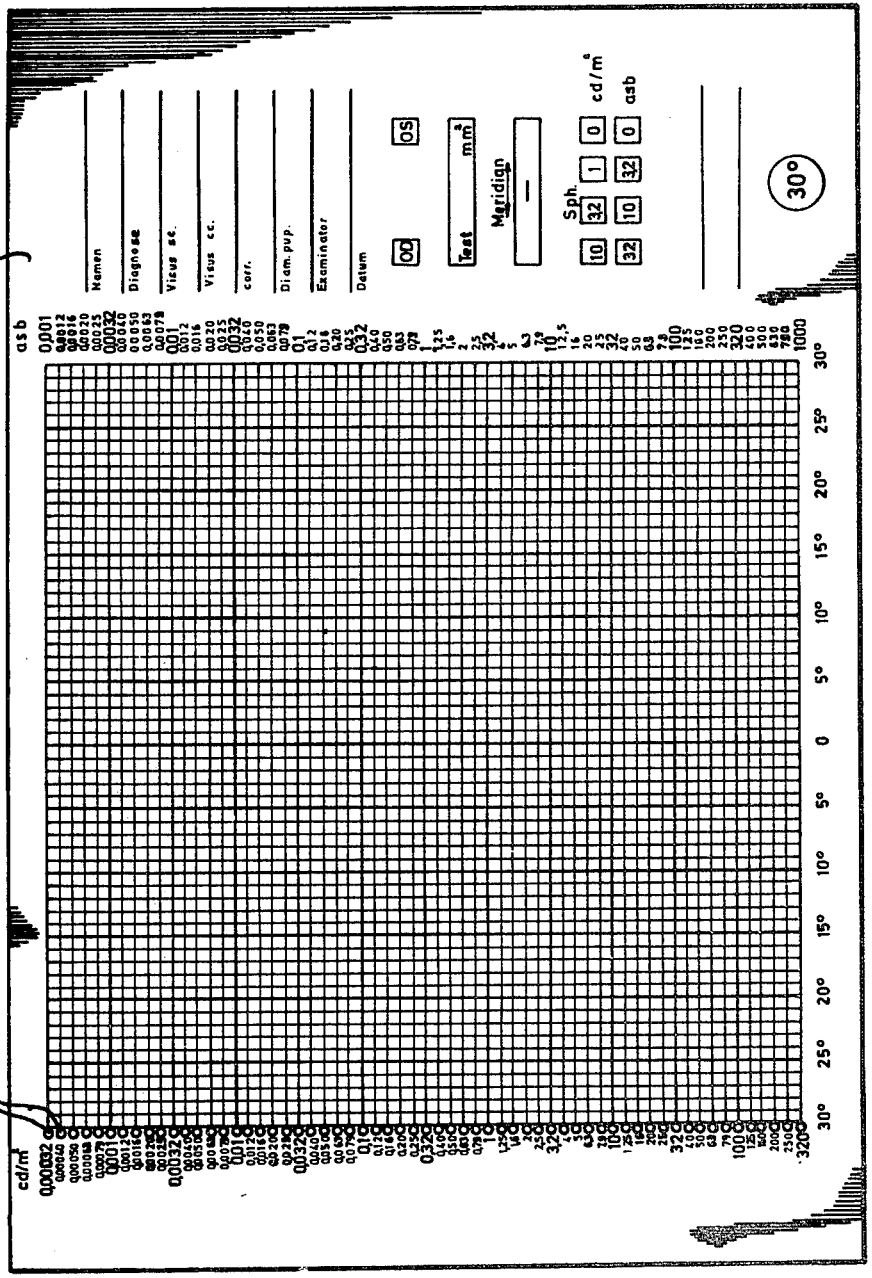
FIG. 7 shows a printed diagram blank which may be utilized in connection with the filter indicator of FIG. 6.

FIG. 7 shows a printed diagram sheet 30 for use in perimetric examination. The graduation of this printed diagram sheet 30 is correlated with the optical indicator 28 and its light-emitting diode 29. In this respect, perforations 31 are located at the sites of the light-emitting diodes 29.

Thus, these filter value variations of the brightness of the projected light beam are indicated to the examiner at the control desk 13 so that the examiner can clearly recognize at all times the brightness value being utilized.

While we have shown and described several embodiments in accordance with the present invention, it is understood that the same is not limited thereto but is susceptible of numerous changes and modifications as known to a person skilled in the art, and We therefore do not wish to be limited to the details shown and described herein but intend to cover all such changes and modifications as are obvious to one of ordinary skill in the art.

We claim:

1. A perimeter for perimetric examinations comprising:

at least one projector for introducing fixed or movable light signals of varying size and brightness on an approximately hemispherical projection area, filter means including a plurality of different filters for attenuating the projected light beam of said projector, drive means for varying said filter means introduced into said light beam, and electronic control means for actuating said drive means for switching said different filters into said projected light beam, either individually or in groups, to selectively increase or decrease the attenuation of said projected light beam and vary brightness of said light signals to introduce a light signal having a predetermined brightness value on said hemispherical projection area, said electronic control means including means for effecting switching of said different filters stepwise in preselected time intervals, and means for effecting a preselected dark interval at which said light beam is not projected to said projection area, said stepwise switching of said different filters occurring during said dark interval.

2. A perimeter according to claim 1, wherein a single stepwise switching of an individual filter is effected during said dark interval.

3. A perimeter according to claim 1, wherein a stepwise switching of a group of a predetermined number of individual filters is effected in succession during said dark interval.

4. A perimeter according to claim 3, wherein said group includes five individual filters being switched in succession during said dark interval.

5. A perimeter according to claim 1, wherein said electronic control means continuously effects said stepwise switching until a predetermined filter is introduced into said projected light beam such that said predetermined brightness value is provided.

6. A perimeter according to claim 1, wherein indicating means are provided for indicating the brightness value of said light signals.

7. A perimeter according to claim 6, wherein said indicating means includes an indicia means for providing a numerical scale of said brightness values and light source means associated with said brightness values for indicating said predetermined brightness value on said numerical scale.

8. A perimeter according to claim 7, wherein said light source means includes a plurality of light-emitting diodes, each of said light-emitting diodes being associated with a given brightness value.

9. A perimeter according to claim 8, wherein a printed diagram sheet for recording results of the examinations by the perimeter is arranged with graduations in association with said numerical scale.

10. A perimeter according to claim 9, wherein said printed diagram sheet covers said light source means and has a plurality of perforations associated with said light-emitting diodes.

11. A perimeter according to claim 7, wherein said electronic control means further controls recording means for recording results of the perimetric examinations 12. A perimeter according to claim 1, further comprising indicating means including an indicia means for providing a numerical scale of said brightness values and light source means associated with said brightness values for indicating said predetermined brightness value on said numerical scale.

13. A perimeter according to claim 12, wherein said light source means includes a plurality of light-emitting diodes, each of said light-emitting diodes being associated with a given brightness value.

14. A perimeter according to claim 13, wherein a printed diagram sheet for recording results of the examinations by the perimeter is arranged with graduations in association with said numerical scale.

15. A perimeter according to claim 14, wherein said printed diagram sheet covers said light source means and has a plurality of perforations associated with said light-emitting diodes.

16. A perimeter according to claim 1, wherein said electronic control means further controls recording means for recording results of the perimetric examinations.

17. In a perimeter including at least one projector for projecting a beam of light to a perimetric surface, filter means including a plurality of filters for attenuating said beam of light, drive means for changing said plurality of filters, and electronic control means for controlling said perimeter, the improvement comprising said electronic control means including means for activating said drive means and switching at least one filter during a predetermined time interval, means for providing light and dark intervals of said projected light, said predetermined time interval occurring only during said dark interval, and means for adjusting the length of said dark interval.

18. A perimeter according to claim 17, wherein a single stepwise switching of one filter is effected during said dark interval.

19. A perimeter according to claim 17, wherein a stepwise switching of a group of a predetermined number of said filters is effected in succession during said dark interval.

20. A perimeter according to claim 19, wherein said group includes five filters being switched in succession during said dark interval.

21. A perimeter according to claim 17, wherein said electronic control means continuously effects stepwise switching of said filters until a predetermined filter is introduced into said projected light beam such that a predetermined brightness value is provided.

22. A perimeter according to claim 17, wherein indicating means are provided for indicating brightness values of said projected beam of light.

23. A perimeter according to claim 22, wherein said indicating means includes an indicia means for providing a numerical scale of said brightness values and light source means associated with said brightness values for indicating said predetermined brightness value on said numerical scale.

24. A perimeter according to claim 23, wherein said light source means includes a plurality of light-emitting diodes, each of said light-emitting diodes being associated with a given brightness value.

25. A perimeter according to claim 24, wherein a printed diagram sheet for recording results of the examinations by the perimeter is arranged with graduations in association with said numerical scale.

26. A perimeter according to claim 25, wherein said printed diagram sheet covers said light source means and has a plurality of perforations associated with said light-emitting diodes.

27. A perimeter according to claim 17, wherein said electronic control means further controls recording means for recording results of perimetric examinations.

* * * * *